United States Patent [19]

Cohen

[11] Patent Number: 5,334,177

[45] Date of Patent: * Aug. 2, 1994

[54] ENHANCED CORE UTILIZATION IN ABSORBENT PRODUCTS

[75] Inventor: Richmond R. Cohen, Warren, N.J.

[73] Assignee: Hercules Incorporated, Wilmington, Del.

[*] Notice: The portion of the term of this patent subsequent to Jul. 19, 2011 has been disclaimed.

[21] Appl. No.: 954,083

[22] Filed: Sep. 30, 1992

Related U.S. Application Data

[63] Continuation-in-part of Ser. No. 941,856, Sep. 8, 1992, which is a continuation of Ser. No. 768,785, Sep. 30, 1991, abandoned.

[51] Int. Cl.$^5$ .................. A61F 13/15; A61F 13/20
[52] U.S. Cl. ................................ 604/378; 604/358; 604/368; 604/366; 604/370
[58] Field of Search ................ 428/361, 364, 391; 604/358, 367–368, 370, 375, 378, 379, 385.1

[56] References Cited

U.S. PATENT DOCUMENTS

| | | |
|---|---|---|
| 2,668,785 | 2/1954 | Jefferson et al. |
| 2,751,962 | 6/1956 | Drummond |
| 2,983,625 | 5/1961 | Schappel |
| 3,388,028 | 6/1968 | Alexander |
| 3,768,480 | 10/1973 | Mesek et al. |
| 4,223,677 | 9/1980 | Anderson |
| 4,397,644 | 8/1983 | Matthews et al. |
| 4,480,000 | 10/1984 | Watanabe et al. |

(List continued on next page.)

FOREIGN PATENT DOCUMENTS

| | | |
|---|---|---|
| 0157649 | 9/1985 | European Pat. Off. |
| 0159671 | 10/1985 | European Pat. Off. |
| 0175481 | 3/1986 | European Pat. Off. |
| 0210968 | 4/1987 | European Pat. Off. |
| 0254476 | 1/1988 | European Pat. Off. |
| 0325416 | 7/1989 | European Pat. Off. |
| 0399511 | 11/1990 | European Pat. Off. |
| 2087240 | 5/1982 | United Kingdom |
| 2124907 | 2/1984 | United Kingdom |

OTHER PUBLICATIONS

"Multi-Layer Nonwovens for Coverstock, Medical and Other End Uses" by Jouko Pirkkanen, Nonwovens World, Nov. 1987.
"Multilayer Diaper Coverstocks Offer New Opportunities" by James Smith, Marketing Technical Specialist, James River Corp. Nonwovens World, Jul. 1988.

Primary Examiner—Randall L. Green
Assistant Examiner—P. Zuttarelli
Attorney, Agent, or Firm—Mark D. Kuller; Tara Gray

[57] ABSTRACT

A core component for use in a fluid-absorbing article, such as a diaper, incontinence pad, catamenial device or the like is described, which core component has a plurality of core zones comprising a zone of vulnerability positioned in said core component for maximum potential exposure to wetting, and at least one additional core zone arranged in an area of reduced potential exposure to initial wetting and in direct or indirect fluid receivable relation from the zone of vulnerability. The zone of vulnerability has a wadding component comprising synthetic fiber of filament and has a greater average pore size and greater average fractional value of fiber volume to fiber surface area than the average pore size and average fractional value of fiber volume to fiber surface area of the wadding component in the at least one additional core zone. When two or more additional core zones are used, the average fractional value of fiber volume-to-fiber surface area and the average pore size within the wadding components of the additional core zones decrease in value from zone to zone with increased distance from the zone of vulnerability and with reduced risk of initial wetting. The wadding component in the zone of vulnerability may be further characterized by having a greater average liquid-solid contact angle than the average liquid-solid contact angle in the wadding components in the additional core zones. A fluid absorbing article and a method for increasing fluid receptivity, fluid storage efficiency, and reduced rewet characteristics utilizing the core component of the invention are also described.

51 Claims, 3 Drawing Sheets

U.S. PATENT DOCUMENTS

| | | |
|---|---|---|
| 4,519,799 | 5/1985 | Sakurai et al. . |
| 4,560,372 | 12/1985 | Pieniak . |
| 4,627,848 | 12/1986 | Lassen et al. . |
| 4,652,484 | 3/1987 | Shiba et al. . |
| 4,673,402 | 6/1987 | Weisman et al. . |
| 4,725,473 | 2/1988 | Van Gompel et al. . |
| 4,755,178 | 7/1988 | Insley et al. . |
| 4,767,586 | 8/1988 | Radwanski et al. . |
| 4,781,962 | 11/1988 | Zamarripa et al. . |
| 4,798,603 | 1/1989 | Meyer et al. . |
| 4,822,668 | 4/1989 | Tanaka . |
| 4,824,596 | 4/1989 | Kitano . |
| 4,837,078 | 6/1989 | Harrington . |
| 4,842,596 | 6/1989 | Kielpikowski et al. . |
| 4,846,842 | 7/1989 | Connolly et al. . |
| 4,882,668 | 11/1989 | Schmid et al. . |
| 4,883,707 | 11/1990 | Newkirk . |
| 4,886,697 | 12/1990 | Perdelwitz et al. . |
| 4,892,534 | 1/1990 | Datta et al. . |
| 4,892,598 | 1/1990 | Stevens et al. . |
| 4,931,357 | 6/1990 | Marshall et al. . |
| 5,004,579 | 4/1991 | Wislinski . |
| 5,033,172 | 7/1991 | Harrington . |
| 5,045,387 | 9/1991 | Schmalt . |
| 5,057,357 | 10/1991 | Winebarger . |

# ENHANCED CORE UTILIZATION IN ABSORBENT PRODUCTS

This is a continuation-in-part of application Ser. No. 07/941,856 filed Sep. 8, 1992 which is a continuation of application Ser. No. 07/768,785 filed Sep. 30, 1991, now abandoned.

FIELD OF THE INVENTION

The present invention relates to a fluid-absorbing core component, a fluid-absorbing article utilizing such component, and a method for making a fluid-absorbing core component.

BACKGROUND OF THE INVENTION

It is generally recognized that success in the marketplace with fluid-absorbing articles such as disposable diapers, incontinence garments or pads, catamenial devices and the like, depends substantially on functional efficiency of the article, as well as comfort to the wearer, appearance and price of the article.

In general, such articles have an efficient fluid-retaining core component, usually comprising one or more layers of absorbent material such as wood pulp, rayon, gauze, tissue or the like, and, in so,he cases, superabsorbent particulate matter or powder (SAP). To protect clothing, and surrounding areas from being wetted and stained by fluids retained in a core component, such articles are generally backed by a fluid-impervious backing component. They also usually possess a nonwoven-type fabric or coverstock material, which defines, at least, the body-contacting surface of the fluid-absorbing article. The nonwoven coverstock material, along with optional intermediate acquisition layers, are relied on to control fluid flow and insulate the wearer from continuous contact with moisture already retained in the core. The facing or coverstock must be pervious to fluids on its body-contacting side to promote rapid transfer of each fluid insult directly into the fluid absorbent core component while, itself, remaining soft, dry and essentially nonabsorbent to aqueous fluids.

The art describes various constructions for core components. Radwanski et. al. in U.S. Pat. No. 4,767,586 describes disposable diapers containing nonwoven webs of cellulosic fiber produced using superimposed layers of material in selected areas. It describes that webs of cellulosic fiber (i.e., for paper making) may be used in different fiber compositional areas. Drummond in U.S. Pat. No. 2,75 1,962 describes producing fibrous products in which coarse and fine denier fiber are incorporated into an integral web.

Marshall et. al. in U.S. Pat. No. 4,931,357 describes forming fibrous material from webs formed of different staple mixtures fed through separate lickerins feedably arranged in parallel axial relation over a conveyor screen or belt. The fiber feed is oriented on the belt by use of baffles to define separate lateral and vertical fiber cross-sections within the resulting web. The web, as shown, is folded over to form a cylindrical-shaped component having a homogeneous external layer.

Anderson in U.S. Pat. No. 4,223,677 describes an absorbent fibrous core structure in which absorbent fibers of less than about 6.35 mm in length are graded by length through the thickness of the absorbent structure.

It is recognized that additional improvements to fluid-absorbing articles are needed to enhance the comfort of the wearer of such articles. Such improvements may include increasing the overall efficiency and liquid acquisition rate of the core component itself, and improving fluid flow control, especially back flow or rewet properties, by varying the make up of core component.

There is a need for a fluid-absorbent core component which has increased fluid receptivity and fluid storage efficiency, and reduced rewet characteristics. There is also a need for a core component which is capable of avoiding the creation of local areas of over-saturation upon insults to the core. It is an object of the invention to provide a core component for use in a fluid-absorbing article which has enhanced fluid retention and control.

SUMMARY OF THE INVENTION

The core component of the present invention has improved fluid control. The core component comprises a plurality of zones including a zone of vulnerability arranged within the core component for maximum potential exposure to initial wetting. There is at least one additional core zone positioned in the core component in direct or indirect fluid receivable relation frown tile zone of vulnerability in an area of reduced potential exposure to initial wetting.

The improved core component of the invention achieves a capillary gradient through the layers of the structure to effect fluid migration away from the fluid-receiving portion of the core component, i.e., the zone of vulnerability, and through the core component in radial, lateral or axial direction. The invention recognizes that a capillary gradient is achieved in several ways: (1) by varying from zone to zone through the core component the denier of the synthetic fiber or filament in the wadding component; (2) by varying the concentration of the fibers in the fiber mix in each zone of the core component wherein tile fiber mix contains one fiber which has a higher average surface area and a lower average volume than the other fiber in the mix; or (3) by varying both the denier of the synthetic fiber and the concentration of the fibers in the fiber mix. In these ways the average volume to surface area ratio and the average pore size changes frown zone to zone. If the concentration of the fibers in the fiber mix changes, in addition to changed pore size, the average liquid-solid contact angle from zone to zone also changes.

DETAILED DESCRIPTION OF THE INVENTION

Figure 1:
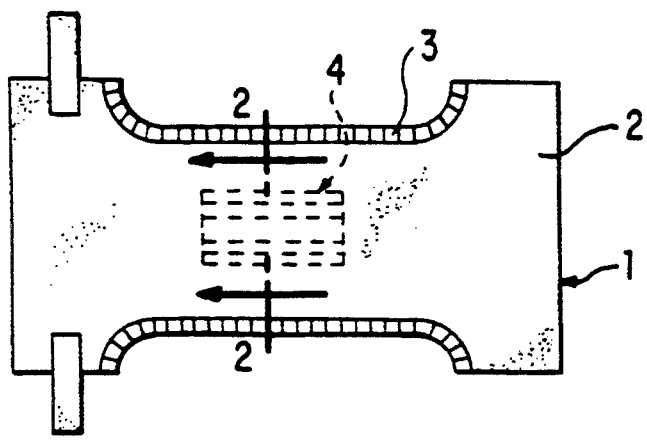
FIG. 1 is a schematic top plan view of a fluid absorbing article showing the core component of the invention in hidden outline.

To achieve the desired capillary gradient, the zone of vulnerability and additional core zones encompass a variety of fiber mixes and core component structures. The zone of vulnerability is usefully characterized by having a greater average pore size than the average pore size of the more wettable additional core zones arranged in direct or indirect fluid-receivable relation from the zone of vulnerability, and may additionally have a greater average liquid-solid contact angle than the average liquid-solid contact angle of the more wettable additional core zones arranged in direct or indirect fluid-receivable relation from such zone of vulnerability. The zone of vulnerability is further usefully characterized by utilizing synthetic fiber or filament having an average fractional value of fiber volume-to-fiber surface area, "volume to surface area" (e.g., $cc/cm^2$) higher than the corresponding average volume to surface area value within the wadding components of the additional core zones arranged in direct or indirect fluid-receivable relation to the zone of vulnerability.

In the additional core zones the average volume to surface area fractional value, the average pore size, and generally the average liquid-solid contact angle, within wadding components of individual additional core zones decrease in value relative to increased distance from the zone of vulnerability and relative to decreased potential exposure to initial wetting. For example, the described values preferably decrease in value in general proportion to increased geometric distance from the zone of vulnerability, and in general proportion to decreased potential exposure to initial wetting. For purposes of the present invention, the average value of the volume to surface area for fiber or fibrillated film in the zone of vulnerability within the above-indicated parameters can vary from about 1 $cc/20,000$ $cm^2$ to about 1 $cc/500$ $cm^2$ or higher, and the corresponding average volume to surface area value within corresponding additional core zones can usefully vary from about 1 $cc/25,000$ $cm^2$ to about 1 $cc/40,000$ $cm^2$ or lower.

In discussing suitable structures of the core component of the invention, a core component laying on a flat surface, with a backing sheet underneath the core component and a coverstock on top will be utilized for illustration. Then, the core component can be described with reference to its x, y and z axes described below. The y-axis is arbitrarily chosen as the axis across the core component in the direction which would correspond to the direction from one leg cuff to a second leg cuff. The x-axis is described as the axis perpendicular to the y-axis. The core component is described as having a "top" which defines a portion of the core component which receives the initial wetting, and is in the plane of the x and y axis, designated the x-y plane; and a "bottom" which defines the portion of the core component adjacent to a fluid-impervious backing. The distance from the top to the bottom of the core component defines the thickness of the core component and describes a z-axis from the top surface. "Radial" shall refer to the perimeter around the zone of vulnerability in the x-y plane. "Lateral" shall refer to the x and y directions from the zone of vulnerability in the x-y plane. "Axial" shall refer to the z-axis through the core component. Fluid migration in the core component of the invention from the zone of vulnerability to the additional core zones shall be described as being generally in the radial direction (i.e., in the x-y plane to the perimeter around the zone of vulnerability), lateral direction (i.e., in the direction of the x or y axis in the x-y plane), or axial direction (i.e., through the core component in the direction of the z-axis). The additional core zones which is the furthest in geometric distance from the zone of vulnerability is said to be the outermost additional core zone.

One embodiment of the instant invention is shown in schematic top plan view in FIG. 1 in use in a fluid absorbing personal article in the general form of an open diaper 1, showing core component 4 in hidden outline, coversheet 2, leg seal cuffs 3, and adhesive tabs (not numbered). The fluid-impervious backing component is not shown in the figure. Coversheet 2 is preferably one formed from a plurality of bonded polyolefin resin fiber or fibrillated film containing webs (not shown) such as treated polypropylene (PP) or polyethylene (PE) staple including copolymers and having homogeneous or mixed denier per filament (dpf) values of a mono- or bicomponent-type fiber. Heat-sealed or cemented thereto is a highly hydrophobic water-impermeable leg seal cuff 3, preferably a topically treated polyolefin nonwoven material, and a core component 4 visible through non-woven coversheet 2, preferably in a rectangular or oval form. The core component of the invention is normally utilized in the form of a rectangular, circular, or oval-shaped body of loosely bonded (or unbonded) wadding, comprising fiber bundles, slivers, fibrillated film and the like, of limited structural strength.

The zone of vulnerability has, as a primary absorbent material, a wadding component comprising synthetic fiber or filament such as polyester or polyolefin-containing fiber inclusive of polypropylene or polyethylene, or copolymers thereof, in an effective amount, here defined as about 25%-100% and preferably about 50%-100% based on the total weight of the zone. The zone of vulnerability can also include, as desired, up to about 75%, preferably 0% to about 50%, of an additional fiber component having a higher fiber surface area and a lower volume, such as cellulose-based fiber. It preferably also contains superabsorbent matter. A useful combination for the zone of vulnerability, for example, includes a polyolefin/cellulose-based staple fiber mixture having a ratio, by weight, of 100%–about 25%/0%–about 75%, preferably 100%–about 50%/0%–about 50%, and up to about 10% of superabsorbent powder or particulate matter (SAP).

The additional core zones have wadding components which comprise fiber mixtures of synthetic fiber or filament and an additional fiber type, or the additional fiber type alone. The additional fiber preferably has a higher fiber surface area and a lower volume than that of the synthetic fiber, for example, such as cellulose-based fiber. Suitable additional core zones contain from about 25% to 100%, preferably about 50% to 100% of an additional fiber type, and up to about 75%, preferably up to about 50% synthetic fiber.

One example of such a core component follows: the zone of vulnerability comprises about 50% synthetic fiber or filament, and about 50% cellulose-based fiber; a first adjacent additional core zone comprises about 20% synthetic fiber and about 80% cellulose-based fiber; and an outermost additional core zone comprises 100% cellulose-based fiber. Superabsorbent particulate matter (SAP) is preferably added to each zone. For example, if 10% SAP is added to the zone of vulnerability the fiber percentage by weights would change to about 45% synthetic fiber arid 45% cellulose based fiber, the balance percentage by weight in SAP. Similarly, the first additional core zone contains 10% synthetic fiber, 70% cellulose-based fiber and 20% SAP; the outermost core zone contains 0% synthetic fiber, 50% cellulose-based fiber and 50% SAP.

Herein the term "denier" shall have its art recognized definition, i.e., it shall mean a measure of filament or thread thickness expressed as grams per 9000 meter length. A suitable fluid absorbent wadding component within the zone of vulnerability, for present purposes, comprises homogeneous or mixed monocomponent or bicomponent synthetic fiber or filament, usefully one having an average dpf value within a range of about 3 to about 50 dpf, preferably about 10.0–40.0. Synthetic fiber or filament in the wadding components within the fluid receivable additional core zones comprise fiber or filaments having average dpf values within a range of about 1–about 40 dpf, preferably 2.0–40. Such fiber or filament may be crimped or uncrimped, as desired.

For purposes of the present invention, the term "synthetic fiber" refers to staple fiber, filament, or fibrillated film selected from the group consisting of polyolefin, polyester and nylons, and include monocomponent and bicomponent fibers. Suitably the fibers or films forming the zones of the core component are modified for conventional processing steps (i.e., cutting, crimping and carding) and for control of flow-through properties, by topical treatment with modifiers or by the inclusion of suitable modifiers within the spun melt itself to increase hydrophilic or antistatic properties. Such suitable fiber processing is disclosed, for instance, in U.S. Pat. No. 5,033,172 of James H. Harrington in which one or more N,N-polyalkoxylated 10-22 carbon fatty amines with up to 60% of 10-22 carbon fatty acid amides are incorporated in the spun melt, and/or treated in accordance with U.S. Pat. No. 5,045,387 of A. C. Schmalz, in which an effective amount of a modifier composition comprising at least one of (a) a component containing alkoxylated ricinoleate with up to about 15%, by weight of modifier composition, of an 18 carbon fatty acid; (b) a corresponding hydrogenated derivative of (a); and (c) a polyalkoxylated polydimethylsiloxane, having up to about 80% by weight of modifier composition, of one or more of component (a), (b), or combination thereof is topically applied onto hydrophobic polyolefin fiber or corresponding fibrillated film.

Also useful, for purposes of the present invention, is the above-indicated incorporation of strategically positioned art-recognized superabsorbent powder or particulate matter within the core zones to improve liquid transport and favor more even and rapid distribution of fluids. Such components are natural absorbents such as guar gum, xanthan gum, or chitin, or are synthesized by the polymerization of acrylic acid, acrylate esters, vinyl alcohol, ethylene oxide, acrylamide, and other vinyl monomers. One of numerous commercially available products of this type is Sumikagel ® S-50 (a product of Sumitomo Company).

Figure 2:
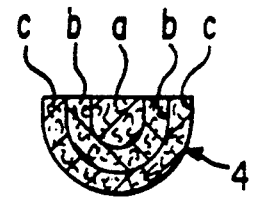
FIGS. 2–4 are schematic cross-section views of alternative embodiments of the core component of the invention taken along line 2—2 of FIG. 1.
Figure 3:
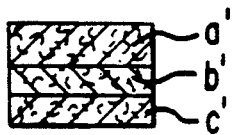
Figure 4:
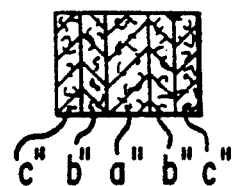

Referring again to the Figures, FIGS. 2–4 represent diagrammatic cross-sections of several suitable variations of core component 4 taken along line 2—2 of FIG. 1, in which the respective zones of vulnerability are respectively shown as (a), (a'), and (a"), and the respective additional core zones as (b) and (c), (b') and (c'), and (b") and (c"). If desired, tile number of additional core zones can be conveniently increased to six or more, for example ten, and is preferably in the range of one to six additional core zones. In high volume or commercial production a core component having one to three additional core zones may be preferable, with those having one additional core zone generally being the simplest to manufacture. The zones are shown in cross-section in suitable, semi-concentric configuration (FIG. 2), in stacked horizontal configuration (FIG. 3), and in vertical/contiguous configuration (FIG. 4). The core zones may be shaped generally as rectangular hexahedrons and positioned in adjacent parallel placement to one another. In each case from the zone of vulnerability, designated by unprimed or primed "a", through additional core zones designated by unprimed or primed "b" and "c," the zones are characterized as having progressively decreased average volume to surface area ratio values, pore size and potentially decreased average liquid-solid contact angles relative. As previously described, these characteristics are obtained, for instance, by varying the fiber mix so as to lower the average dpf of the synthetic fiber, and by varying the average liquid-solid contact angle by increasing the concentration of one or more supplemental fibers, preferably fibers having a lower average volume and a higher average fiber surface area, such as a cellulose-based fiber.

In FIG. 2, (a) represents a centrally located zone of vulnerability, preferably one containing about 25%–100%, preferably about 50%–100% of a synthetic thermoplastic fiber preferably topically or otherwise treated for working and retained hydrophilic properties. Such fiber, as above noted, can be a spun and treated polyolefin resin, resin mix or copolymers thereof (i.e., PP/PE) having relatively high average dpf values within the above-indicated range, and combined with about 0%–about 75%, preferably 0%–about 50%, by weight of cellulose-based fiber, and SAP powder or particulate matter as above described.

Additional core zones, (b) and (c) of FIG. 2, in that order, represent individual homogeneous zones comprising fibrous absorbent material having a progressively smaller average fiber volume and higher average fiber surface area and a progressively smaller average pore size, and, if the concentration of fibers in the fiber mix also change, a lower average liquid-solid contact angle as the relative geometric distance from zone (a) increases. Zones (a) (b) and (c) can be individually bonded (or unbonded), or bonded "in toto" using conventional bonding techniques, such as through-air thermal bonding, calender bonding, needle-punching, and water jet entanglement. The use of thermal bonding requires the presence of a binder fiber in the zones of the core component, such as a sheath-core bicomponent fiber having a low melting sheath, a polyethylene fiber, or other low melting polymers. The embodiment illustrated in FIG. 2 demonstrates a structure in which fluid migration from the zone of vulnerability occurs in both the lateral and axial directions. The embodiment illustrated in FIG. 3 demonstrates fluid migration in the axial direction. The embodiment illustrated in FIG. 4 demonstrates fluid migration in the lateral direction.

Figure 6:
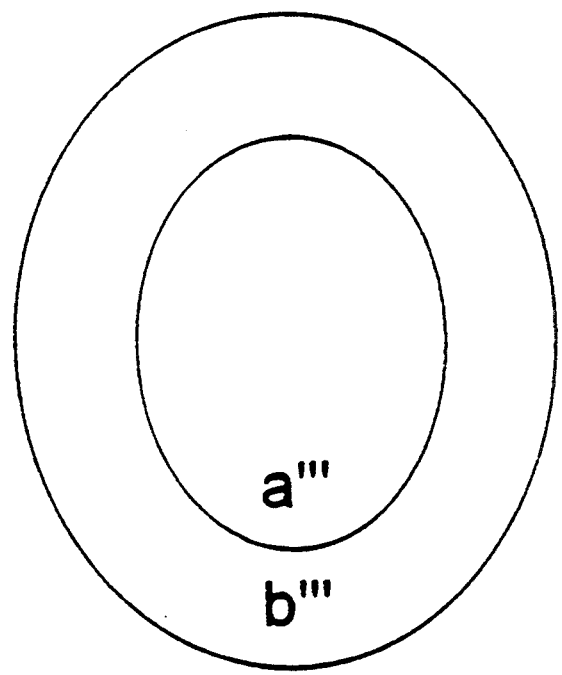
FIGS. 6–7 are schematic top plan views of alternative embodiments of the invention.
Figure 7:
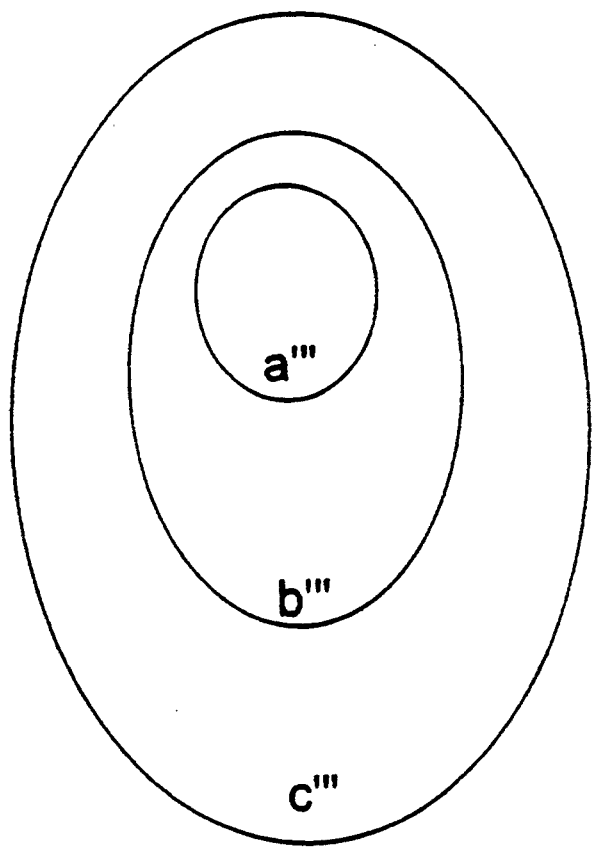

The embodiments illustrated in FIGS. 6 and 7 demonstrate fluid migration in the radial direction. A particularly suitable embodiment for the core component of the invention is shown in schematic top plan view in FIG. 6 in which a zone of vulnerability (a''') is radially surrounded by a single additional core zone (b'''). The top and bottom of zone of vulnerability (a''') are not surrounded by the additional core zone (b'''), and a bottom view of this configuration (not shown) would show essentially the stone configuration as that shown in FIG. 6.

FIG. 7 illustrates an alternative embodiment in schematic top plan view of the radial configuration in which another additional core zone (c''') is added to the structure in which additional core zone (c''') is formed radially around additional core zone (b'''). The radial configurations illustrated in FIGS. 6 and 7 also accommodate any number of additional core zones, preferably from one to six additional core zones, preferably one or two additional core zones, and most preferably one additional core zone.

Encouraging fluid migration in several directions is achieved by combining the structures described. An alternative embodiment of the radial configuration in FIG. 6, for example, comprises stacking a first radial structure upon a second radial structure (not shown) in which the zone of vulnerability of the second radial structure has a reduced percentage by weight of synthetic fiber than the percentage by weight of synthetic fiber in the zone of vulnerability of the first radial structure to create a gradient in both the radial and axial direction.

Figure 5A:
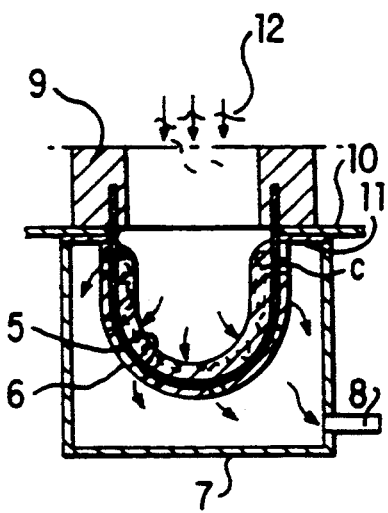
FIGS. 5A, 5B and 5C exemplify progressive steps representing a suitable technique for forming the core zones of the core component of the invention.

FIG. 5A represents, in schematic cross-section view, a step or stage in a process suitable for producing zoned core components within the scope of the present invention, in which a continuous flexible screen or belt 5 is supported from movable support elements 9 having end-wise attached flanges 10 slideably resting on corresponding support flanges 11 at the top of a "U" shaped perforated forming trough 6 forming an upper surface of suction box 7. As shown, one core layer, corresponding, for instance, to additional core zone (c) of FIG. 2 has been formed from an air entrained fiber mix 12 supplied frown above (see arrows) through twin lickerins axially arranged in machine direction and a mixing zone (not shown). The entrained fiber is shown to be adhered to the corresponding "U" shaped flexible screen or belt 5 with the aid of a partial vacuum obtained through vacuum exhaust pipe 8 on the reverse side of the belt and trough 6.

Figure 5B:
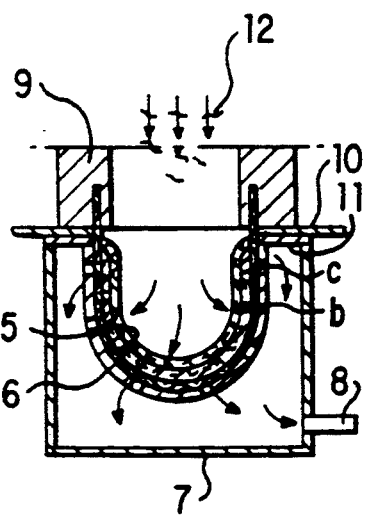

An additional core zone, here represented in FIG. 5B as layer (b), is conveniently applied at a downstream station, using different fiber, or fiber/particulate mixtures to obtain a core zone of higher fiber volume and lower fiber surface area (i.e., a numerically higher volume to surface area value) and a larger average pore size, and potentially a larger average liquid-solid contact angle than laid down in zone (c).

Figure 5C:
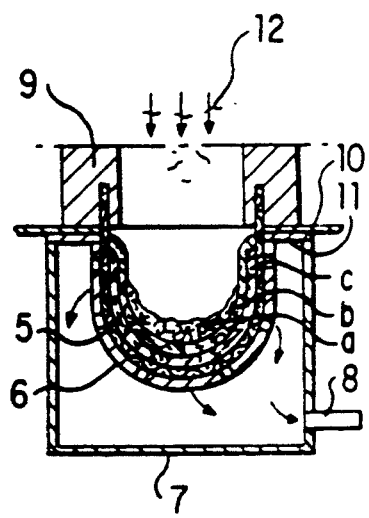

FIG. 5C schematically represents a cross-section at a further downstream station in which the zone of vulnerability or (a) core zone is formed. As shown, the air-entrained fiber or particulate matter making up such zone is applied from above in the general manner of the previous upstream stations as shown in FIGS. 5A and 5B, however, the (a) zone can also be separately laid down "in toto" as a compiled fiber or filament mass as webs, or even as fibrillated film, and the entire wadding optionally bonded together using sonic, thermal, laser or similar conventional bonding techniques (not shown).

The dimensions of each core zone vary according to the fluid-absorbing article and the size of the particular article in which the core component is utilized. For example, the size of each zone depends upon the structure of the core component and the number of additional core zones utilized. A suitable zone of vulnerability has a diameter within the range of about 5 cm to about 10 cm. The zone of vulnerability ranges in thickness from about 2 mm to about 2 cm. The additional core zones range in thickness from about 2 mm to about 2 cm. Additional core zones surrounding the zone of vulnerability in the radial or lateral direction represent increments from the zone of vulnerability in the x-y plane. The increments of the additional core zones range in size from about 0.5 cm to about 20 cm.

EXAMPLE I

A. Three test diaper cores, identified as T-1, T-2 and T-3 and having the general semi-concentric configuration as described in FIG. 2, are formed from sequentially-applied mixtures of air entrained 18 dpf (0.75 inch staple) polypropylene and cellulose fluff pulp fiber (obtained from Georgianier Wood Pulp softwood bleached Kraft from ITT Rainier Co.). The mixtures are applied at five separate stations onto a movable screen or belt in the manner generally described with respect to FIGS. 5A–5C. The resulting unbonded zones are sequentially laid down in about 1"-thick layers having the following concentrations (in weight percent) of polypropylene/cellulose: 0/100, 10/90, 15/85, 25/75 and 50/50 (zone of vulnerability).

The test cores, in toto, contain 23 weight percentage (23 wt. %) polypropylene staple with a density of about 0.045 gm/cc. The test cores are then topped with identical polypropylene nonwoven coverstock and tested for Liquid Acquisition and Rewet characteristics (Table I) using a pressure-driven GATS (Gravimetric Absorbency Testing System) with GATS II test equipment from M/K Systems Inc. of Danvers, Mass. A raised (15 cm) liquid reservoir is feedably connected by tubing (for upward flow) beneath a single-holed simple platform. The test core and a coverstock are placed thereon above the hole under 0.1 psia. A flow valve is opened for one (1) second and reservoir weight loss recorded. The reservoir weight loss is equated to the weight gain by the test core, and the weight gain divided by tinge provides initial acquisition rate data.

The rewet test is effected by obtaining an 80% core saturation using as synthetic urine, a 53 dyne/cm dilute saline-surfactant solution obtained from Pluronic® 10-R-8 surfactant from BASF Inc. After five (5) minutes the test core is removed and covered with a second preweight dry bonded core and pressed (0.5 psi) for two (2) minutes, the increase in weight of the dry-bonded core is reported as rewet in grams.

As a control, Example IA is repeated but using identical polypropylene/cellulose staple mixtures at each zone application station to obtain uniformly-distributed fiber mix throughout the core at a density of about 0.045 gm/cc and a total content of polypropylene staple of about 23 wt. %. The control cores, identified as C-1, C-2 and C-3, are tested for Acquisition Rate and Rewet Properties as before and the results reported as an average in Table I below.

As a further control, three cores, identified as C-4, C-5 and C-6 are prepared using 100 weight percent of the same batch cellulose as that used in the previous example in each zone to obtain a core of about the same density and weight. These control cores are identically tested for Acquisition Rate and Rewet Properties and the results reported as an average in Table I below. As a comparison for Acquisition Rate, it is noted that maximum unimpeded flow is 10.7 ml/second.

TABLE I

| Core Sample # | Acquisition Rate ml/second (av.) | Rewet (gm) (av.) |
| --- | --- | --- |
| T-1, T-2, T-3 | 9.7 | 7.9 |
| C-1, C-2, C-3 | 8.8 | 8.0 |
| C-4, C-5, C-6 | 8.1 | 9.9 |

B. Example IA is repeated in core samples T-4, T-5 and T-6, using 15 dpf 0.75" polyester staple in place of polypropylene staple. The cores are identically tested as before and the averaged test results reported in Table II below. Example IA is repeated with control cores C-7, C-8 and C-9, in which the same total amounts of polyester (PET) and identical weight percentage of PET/cellulose as used in T-4, T-5 and T-6 are applied at each zone to obtain a uniform staple distribution through the cores. The cores are tested as before and the averaged test results reported in Table II below as averages. Again, it is noted that maximum unimpeded flow rate is 10.7 ml.sec.

TABLE II

| Core Sample # | Acquisition Rate ml/second (av.) |
| --- | --- |
| T-4, T-5, T-6 | 10.5 |
| C-7, C-8, C-9 | 8.7 |

Examples IA and IB are repeated but with the addition of 5 weight percent of Sumikagel® S-50 (SAP) within the zone of vulnerability and 5 weight percent within the outermost zone (the first laid down in FIG. 5A). Rewet determinations are carried out as before and the averaged test results reported in Table III as average values in comparison with Example IA and IB values.

TABLE III

| Core Sample # | Rewet (no SAP) (gm) | Rewet (with SAP) (gm) |
| --- | --- | --- |
| T-1, T-2, T-3 | 7.9 | 5.5 |
| C-1, C-2, C-3 | 8.0 | 6.3 |

EXAMPLE II

Test diaper cores, identified as T-7, T-8, and T-9 and having the general radial configuration as described in FIG. 6, are formed from mixtures of air entrained 20 dpf (0.75 inch staple) polypropylene and cellulose fluff pulp (obtained from Georgianier Wood Pulp bleached Kraft from ITT Rainier Co.). The following concentrations (in weight percent) of polypropylene/cellulose: 0/100 and 50/50 (zone of vulnerability) are utilized. A first additional core zone comprising an approximately one (1) inch layer of 100% cellulose is formed, and a hole of approximately 1½ to 2" in diameter is punched and removed from a central area of the additional core zone. A second layer of the 50/50 concentration is formed, and a generally circular form of approximately 1½ to 2 inches in diameter, representing the zone of vulnerability, is removed froth the second layer. The circular form is inlaid into the hole punched in the first layer to form a core component with a zone of vulnerability and one additional core zone.

The test cores, in toto, contain 33 weight percentage (33 wt. %) polypropylene staple with a density of about 0.05 gm/cc. The test cores are then topped with identical polypropylene nonwoven coverstock and tested for Liquid Acquisition (Table I) using a pressure-drive GATS (Gravimetric Absorbency Testing System) with GATS II test equipment from M/K Systems Inc. of Danvers, Mass. as described in Example I.

As a control, the example above is repeated but using identical polypropylene/cellulose staple mixtures at each zone application station to obtain uniformly-distributed fiber mix throughout the core at a density of about 0.05 gm/cc and a total content of polypropylene staple of about 33 wt. %. The control cores, identified as C-10, C-11 and C-12 are tested for Acquisition Rate as before and the results reported as an average in Table IV below.

As a further control, three cores, identified as C-13, C-14 and C-15 are prepared using 100 weight percent of the stone batch cellulose in each zone to obtain a core of about the same density and weight. These control cores are identically tested for Acquisition Rate and the results reported as an average in Table IV below. As a comparison for Acquisition Rate, it is noted that maximum unimpeded flow is 10.7 ml/second.

TABLE IV

| Core Sample # | Acquisition Rate |
| --- | --- |
| T-7, T-8, T-9 | 9.16 ml/sec (av.) |
| C-10, C-11, C-12 | 7.81 ml/sec (av.) |
| C-13, C-14, C-15 | 7.35 ml/sec (av.) |

What is claimed is:

1. A core component for use in a fluid-absorbing article having a plurality of zones comprising:
   (a) a zone of vulnerability positioned in said core component for maximum exposure to initial wetting, the zone of vulnerability having a wadding component comprising synthetic fiber; and
   (b) at least one additional core zone in the core component having a wadding component and arranged in the core component in an area of reduced potential exposure to initial wetting and in fluid-receivable relation to said zone of vulnerability;
   wherein the wadding component in the zone of vulnerability has (1) a greater average pore size than the average pore size of the wadding components in the at least one additional core zone and (2) a higher average fractional fiber volume-to-fiber surface area value than the average fractional fiber volume-to-fiber surface area in the wadding component of the at least one additional core zone.

2. The core component according to claim 1 wherein the at least one additional core zone is positioned in a radial configuration around the zone of vulnerability.

3. The core component according to claim 1 wherein the wadding component in the zone of vulnerability comprises fiber having an average dpf value within a range of about 3 to about 50 dpf.

4. The core component according to claim 1 wherein the average fractional value of fiber volume to fiber surface as in the zone of vulnerability is in a range of about 1 cc/20,000 cm² to about 1 cc/500 cm².

5. The core component according to claim 1 wherein the at least one additional core zone contains from about 0% to 75% by weight of synthetic fiber and about 25% to 100% by weight of a cellulose-based fiber.

6. The core component according to claim 1 wherein the wadding component in the at least one additional core zone comprises fiber having an average dpf value in a range of about 1 to about 40 dpf.

7. The core component according to claim 1 wherein the average fractional value of fiber volume-to-fiber surface area in the at least one additional core zone is in a range of about 1 cc/25,000 cm² to about 1 cc/40,000 cm².

8. The core component according to claim 1 wherein the zone of vulnerability is bonded, and is bonded to the at least one additional core zone, by a bonding technique selected from the group consisting of through-air thermal bonding, calender bonding, needle-punching, and water jet entanglement.

9. The core component according to claim 1 wherein the core component comprises one additional core zone.

10. A fluid-absorbing article comprising, in combination, the core component of claim 1 arranged within at least a fluid permeable coverstock and a fluid impervious backing layer.

11. The core component according to claim 1 wherein the zone of vulnerability comprises from about 25% to 100% by weight of fiber selected from the group consisting of monocomponent and bicomponent polyolefin, polyester and nylon.

12. The core component according to claim 11 wherein the at least one additional core zone contains from about 0% to 75% by weight of synthetic fiber and about 25% to 100% by weight of a cellulose-based fiber.

13. The core component of claim 1 further comprising superabsorbent powder or particulate matter in the zone of vulnerability.

14. The core component of claim 13 further comprising superabsorbent powder or particulate matter in the at least one additional core zone.

15. The core component according to claim 1 wherein the wadding component in the in the zone of vulnerability has a greater average liquid-solid contact angle than the average liquid-solid contact angle in the wadding component of the at least one additional core zone.

16. The core component according to claim 15 wherein the zone of vulnerability comprises from about 25% to 100% by weight of fiber selected from the group consisting of monocomponent and bicomponent polyolefin, polyester and nylon; wherein the wadding component in the zone of vulnerability comprises fiber having an average dpf value within a range of about 3 to about 50 dpf; wherein the average fractional value of fiber volume to fiber surface area in the zone of vulnerability is in a range of about 1 cc/20,000 cm² to about 1 cc/500 cm²; wherein the at least one additional core zone contains from about 0% to 75% by weight of synthetic fiber and about 25% to 100% by weight of a cellulose-based fiber; wherein the wadding component in the at least one additional core zone comprises fiber having an average dpf value in a range of about 1 to about 40 dpf; wherein the average fractional value of fiber volume-to-fiber surface area in the at least one additional core zone is in a range of about 1 cc/25,000 cm² to about 1 cc/40,000 cm²; and wherein the zone of vulnerability is bonded, and is bonded to the at least one additional core zone, by a bonding technique selected from the group consisting of through-air thermal bonding, calender bonding, needle-punching, and water jet entanglement.

17. The core component according to claim 16 wherein at least one additional core zone is positioned in a radial configuration around the zone of vulnerability.

18. The core component according to claim 17 wherein the core component comprises one additional core zone.

19. The core component of claim 15 wherein the zone of vulnerability comprises a wadding component comprising synthetic fiber or filament selected from the group consisting of polyester and polyolefin fibers and filaments and cellulose fiber; and the at least one additional core zone comprises a wadding component comprising cellose-based fiber.

20. The core component of claim 19 wherein the at least one additional core zone further comprises synthetic fiber.

21. The core component of claim 20 further comprising superabsorbent powder or particulate matter in the zone of vulnerability.

22. The core component of claim 21 further comprising superabsorbent powder or particulate matter in the at least one additional core zone.

23. The core component of claim 19 further comprising superabsorbent powder or particulate matter in the zone of vulnerability.

24. The core component of claim 23 further comprising superabsorbent powder or particulate matter in the at least one additional core zone.

25. A core component for use in a fluid-absorbing article having a plurality of zones comprising:
(a) a zone of vulnerability positioned in said core component for maximum potential exposure to initial wetting, said zone of vulnerability having a wadding component comprising synthetic fiber or filament; and
(b) a plurality of additional core zones in the core component each having a wadding component and arranged in the core component in an area of reduced potential exposure to initial wetting and in fluid-receivable relation to said zone of vulnerability;
wherein (A) the wadding component in the zone of vulnerability has (1) greater average pore size than the average pore size of the wadding components within the additional core zones and (2) a higher average fractional value of fiber volume-to-fiber surface area than the average fractional value of fiber volume-to-fiber surface area within the wadding components of the additional core zones and (B) the average fractional value of fiber volume-to-fiber surface area and the average pore size within the wadding components of the additional core zones decrease in value frown zone to zone relative to increased distance from the zone of vulnerability and to decreased potential exposure to initial wetting.

26. The core component according to claim 25 wherein the additional core zones are positioned in radial configuration about the zone of vulnerability.

27. The core component according to claim 25 wherein the additional core zones are positioned in a semi-concentric configuration about the zone of vulnerability.

28. The core component according to claim 25 wherein the wadding component in the zone of vulnerability has a greater average liquid-solid contact angle than the average liquid-solid contact angle in the wadding components of the additional core zones, and the average liquid-solid contact angle within the additional core zones decreases in value frown zone to zone relative to increased distance from the zone of vulnerability and to decreased potential exposure to initial wetting.

29. The core component according to claim 28 wherein the additional core zones are positioned about the zone of vulnerability in semi-concentric configuration.

30. The core component according to claim 28 wherein the zone of vulnerability and the additional core zones form generally rectangular hexahedrons in adjacent parallel placement to one another.

31. The core component according to claim 28 wherein the additional core zones are positioned in radial configuration around the zone of vulnerability.

32. The core component according to claim 28 wherein the wadding component of the zone of vulnerability comprises about 25% to 100% by weight of polyolefin or polyester staple fiber or filament.

33. The core component according to claim 28 wherein the wadding component of the zone of vulnerability comprises about 50% to 100% by weight of polyolefin or polyester staple fiber or filament.

34. The core component according to claim 28 wherein the zone of vulnerability comprises from about 0% up to about 50% by weight of a cellulose-based fiber.

35. The core component according to claim 28 wherein the additional core zones comprise from about 25% to about 100% by weight of a cellulose-based fiber.

36. The core component according to claim 28 wherein the additional core zones comprise from about 50% to 100% by weight of a cellulose-based fiber.

37. The core component according to claim 28 wherein the wadding components within the additional core zones comprise fiber or filament having an average dpf value within a range of about 2.0 to 40 dpf.

38. A fluid-absorbing article comprising, in combination, the core component of claim 28 arranged within at least a fluid permeable coverstock and a fluid impervious backing layer.

39. The core component of claim 28 wherein the zone of vulnerability comprises a wadding component comprising synthetic fiber or filament selected from the group consisting of polyester and polyolefin fibers and filaments and cellulose fiber; and the at least one additional core zone comprises a wadding component comprising cellose-based fiber.

40. The core component of claim 39 further comprising superabsorbent powder or particulate matter in the zone of vulnerability.

41. The core component of claim 28 further comprising superabsorbent powder or particulate matter in the zone of vulnerability.

42. The core component of claim 41 further comprising superabsorbent powder or particulate matter in the at least one additional core zone.

43. The core component according to claim 28 wherein the zone of vulnerability comprises about 25% to 100% by weight of fiber selected from the group consisting of monocomponent and bicomponent polyolefin, polyester and nylon, and about 75% to 0% by weight of cellulose-based fiber.

44. The core component according to claim 43 wherein the additional core zones comprise from about 25% to about 100% by weight of a cellulose-based fiber.

45. The core component according to claim 44 wherein the additional core zones are positioned in a radial configuration about the zone of vulnerability.

46. The core component according to claim 44 wherein the additional core zones are positioned in a semi-concentric configuration about the zone of vulnerability.

47. A core component for use in a fluid-absorbing article for enhanced fluid retention and control having a plurality of zones characterized by:
    (a) a zone of vulnerability positioned in said core component for maximum exposure to initial wetting, said zone of vulnerability having a wadding component comprising synthetic fiber or filament; and
    (b) a plurality of additional core zones in the core component each having a wadding component and arranged in the core component in areas of reduced potential exposure to initial wetting and in fluid-receivable relation from said zone of vulnerability;
    wherein the wadding component in the zone of vulnerability is characterized by (1) a greater average pore size and greater average liquid-solid contact angle than the average pore size and average liquid-solid contact angle of the wadding components within the additional core zones and (2) a higher average fractional value of fiber volume to fiber surface area than the average fractional value of fiber volume to fiber surface area within the wadding components of the additional core zones; and wherein the average fractional value of fiber volume to fiber surface area, the average liquid-solid contact angle, and average pore size within the wadding components of said additional core zones decrease in value from zone to zone in general proportion to increased geometric distance from said zone of vulnerability and corresponding decreased exposure to initial wetting.

48. A fluid-absorbing article comprising, in combination, the core component of claim 47 arranged within at least a fluid permeable coverstock and a fluid impervious backing layer.

49. The core component of claim 47 wherein the zone of vulnerability comprises a wadding component comprising synthetic fiber or filament selected from the group consisting of polyester and polyolefin fibers and filaments and cellulose fiber; and the at least one additional core zone comprises a wadding component comprising cellose-based fiber.

50. The core component of claim 47 further comprising superabsorbent powder or particulate matter in the zone of vulnerability.

51. The core component of claim 50 further comprising superabsorbent powder or particulate matter in the at least one additional core zone.

* * * * *

UNITED STATES PATENT AND TRADEMARK OFFICE
CERTIFICATE OF CORRECTION

PATENT NO. : 5,334,177
DATED : August 2, 1994
INVENTOR(S) : Richmond R. Cohen It is certified that error appears in the above-identified patent and that said Letters Patent is hereby corrected as shown below:

In the Claims, Col. 10, line 48, "surface as in the zone" should read --surface area in the zone--;

Col. 12, lines 46 and 47, "positioned in radial" should read --positioned in a radial--; and Col. 13, lines 2 and 3, "positioned in radial" should read --positioned in a radial--.

Signed and Sealed this

Eighth Day of November, 1994

*Attest:*

BRUCE LEHMAN

*Attesting Officer*     *Commissioner of Patents and Trademarks*